United States Patent [19]

Li et al.

[11] Patent Number: 4,458,835

[45] Date of Patent: * Jul. 10, 1984

[54] SURGICAL STAPLING CONTROL MEANS

[75] Inventors: Lehmann K. Li, Fairfield, Conn.; Jay E. Campbell, Upper Black Eddy; Richard H. Reichmann, Churchville, both of Pa.

[73] Assignee: American Cyanamid Company, Stamford, Conn.

[*] Notice: The portion of the term of this patent subsequent to Jul. 5, 2000 has been disclaimed.

[21] Appl. No.: 321,038

[22] Filed: Nov. 13, 1981

Related U.S. Application Data

[63] Continuation-in-part of Ser. No. 191,653, Sep. 26, 1980, Pat. No. 4,391,402, which is a continuation-in-part of Ser. No. 153,229, May 27, 1980, abandoned.

[51] Int. Cl.³ .............................................. A61B 17/04
[52] U.S. Cl. ..................................... 227/121; 227/19; 227/DIG. 1; 128/334 R; 72/410
[58] Field of Search ................. 72/410; 128/334 R; 227/DIG. 1, 19, 83, 107, 114, 115, 116, 119, 227/120, 121, 139, 149, 156

[56] References Cited

U.S. PATENT DOCUMENTS

| 1,271,548 | 7/1918 | Doig | 227/121 |
| 2,707,783 | 5/1955 | Sullivan | 72/410 |
| 3,873,016 | 3/1975 | Fishbein | 227/83 |
| 3,905,535 | 9/1975 | Novak et al. | 227/120 |
| 4,108,306 | 8/1978 | Samuels et al. | 227/121 X |
| 4,109,844 | 8/1978 | Becht | 227/120 |
| 4,179,057 | 12/1979 | Becht et al. | 227/120 X |
| 4,196,836 | 4/1980 | Becht | 227/19 |
| 4,202,480 | 5/1980 | Annett | 227/121 X |
| 4,204,623 | 5/1980 | Green | 227/121 X |

Primary Examiner—Paul A. Bell
Attorney, Agent, or Firm—Charles F. Costello, Jr.

[57] ABSTRACT

A surgical stapling control means has been invented. The control means comprises a handle; a trigger pivotally attached and on compression internal to said handle; a staple forming means contained in the forward portion of said handle; a pad contained on the rearward portion of said handle; a retainer attached to the rearward portion of said trigger to coordinate with said pad; at least one guide pin attached to the initial end of said retainer; and guide means adjacent the rearward portion of said handle to coordinate with and provide tension to said guide pin.

6 Claims, 7 Drawing Figures

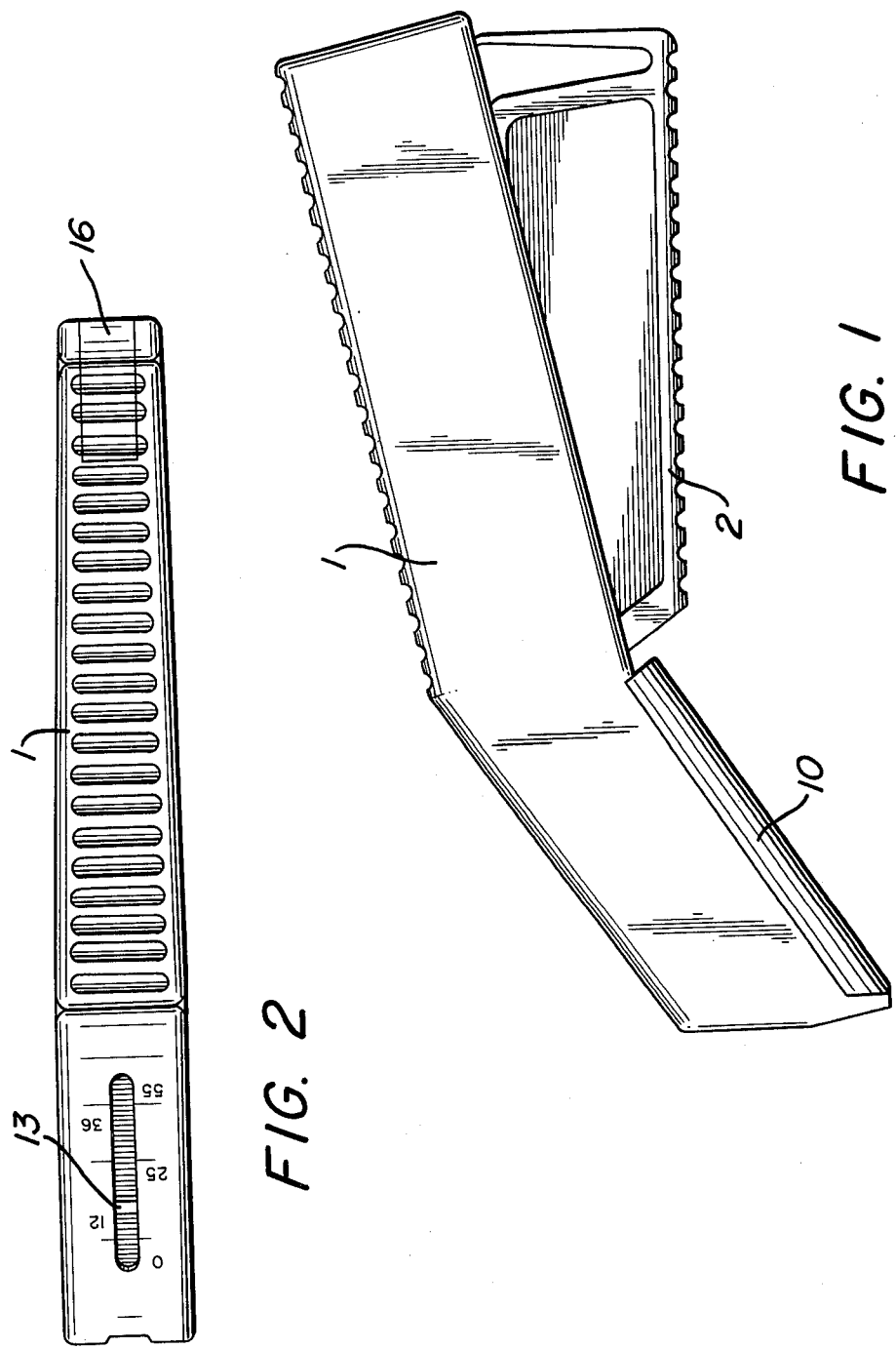

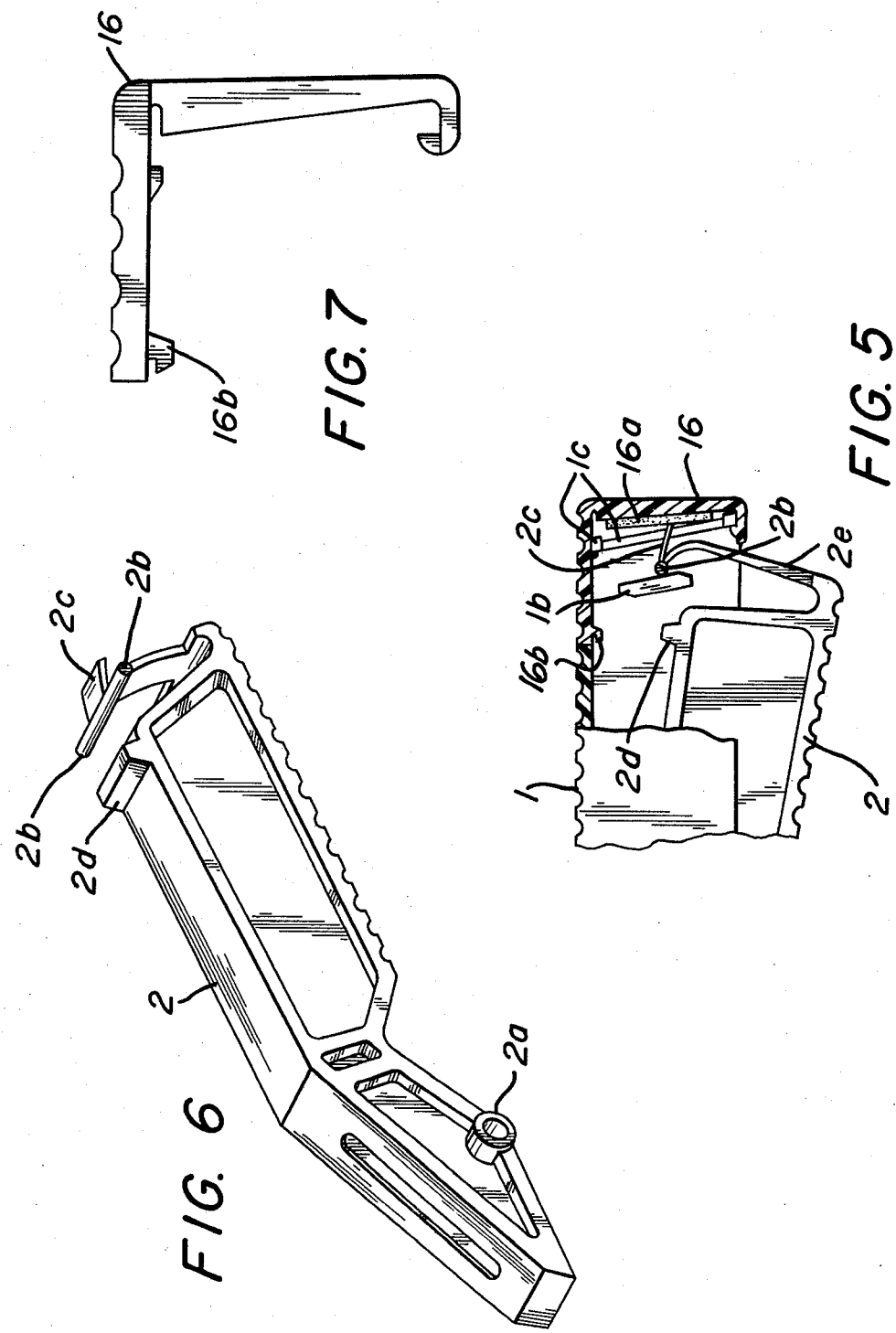

4,458,835

SURGICAL STAPLING CONTROL MEANS

CROSS REFERENCE TO RELATED APPLICATIONS

This is a continuation-in-part application of U.S. application Ser. No. 191,653 filed Sept. 26, 1980, now U.S. Pat. No. 4,391,402 which is a continuation-in-part application of U.S. application Ser. No. 153,229 filed May 27, 1980 now abandoned.

BACKGROUND AND SUMMARY OF THE INVENTION

This invention relates to a surgical stapling control means which prevents the trigger in a stapling instrument from partially forming a staple and then returning to its relaxed position to pick up the next staple. This invention also relates to a stop contained on the rearward top portion of a surgical stapling instrument trigger. The stop arrests the compression force of the trigger into the handle.

The Applicants are not aware of any prior art references which in their judgements as persons skilled in the art would anticipate or render obvious the control means of this invention. However, to develop the background of the invention and to establish the state of the art, the following references are cited. U.S. Pat. Nos. 4,196,836 and 3,873,016 disclose a stapling control means and U.S. Pat. No. 4,179,057 discloses a stapling instrument including a handle lug. The lug acts as a stop for the trigger. These patents are incorporated by reference.

The control means of this invention prevents the trigger from returning to its initial position if the compression is interrupted. This has the advantage of preventing a second staple from being formed on the anvil before a first staple is separated from the instrument. Another advantage of the control means is interrupted stapling. The surgeon can stop the compression of the trigger into the handle to realign the instrument over the wound site. Thus the possibility of a perfect stapling procedure is greatly enhanced. Finally, the control means are automatically disengaged on completely compressing the trigger. The control means do not have to be manually reset after a single staple is formed and separated from the instrument.

A surgical stapling control means has been invented. The control means comprises a handle; a trigger pivotally attached and on compression internal to said handle; a staple forming means contained in the forward portion of said handle; a retainer attached to the rearward portion of said trigger to coordinate with said pad; at least one guide pin attached to the initial end of said retainer; and guide means adjacent the rearward portion of said handle to coordinate with and provide tension to said guide pin. On partially compressing said trigger, said guide means provide tension on said guide pin and said retainer engages said pad. On completely compressing said trigger, said guide pin crosses over the top of said guide means causing said retainer to be disengaged from said pad.

Other embodiments of a stapling control means described above are: wherein said guide means are two cams attached to each side of said handle; wherein two guide pins coordinate with said cams; wherein said pad is contained between a flanged opening and a handle cover; and wherein the surface of the flange adjacent to said pad is textured.

The stapling control means described above can also contain an indicator. The indicator has a terminal end visible in said handle and an initial end carried by said forming means. On releasing said trigger, said indicator advances to indicate the number of staples remaining in a surgical stapling instrument.

An improved surgical stapling instrument has also been invented. The stapling instrument comprises a handle; a trigger pivotally attached and on compression internal to said handle; and a staple forming means contained in the forward portion of said handle. On compressing said trigger into said handle a staple is formed by said forming means. On releasing said trigger and advancing said instrument said formed staple separates from said instrument and said trigger returns to its initial position. The improvement comprises a stop contained on the rearward top portion of said trigger. The stop arrests the compression force of the trigger into the handle.

A method of closing a wound and a method of connecting skin or fascia have also been invented. The methods comprise joining the adjacent edges of said wound or said skin or fascia; placing a stapling instrument described above adjacent said wound or said skin or fascia; compressing said trigger into said handle; and releasing said trigger and advancing said instrument, whereby a formed staple is placed between said edges.

DESCRIPTION OF THE DRAWINGS

FIGS. 1 and 2 are side and top views respectively of the stapling instrument;

FIG. 5 is a broken sectional view of the stapling instrument control means showing the trigger in partial compression;

FIG. 6 is a perspective view of the instrument trigger;

FIG. 7 is a side view of the handle cover;

DESCRIPTION OF THE PREFERRED EMBODIMENT

Figure 3:
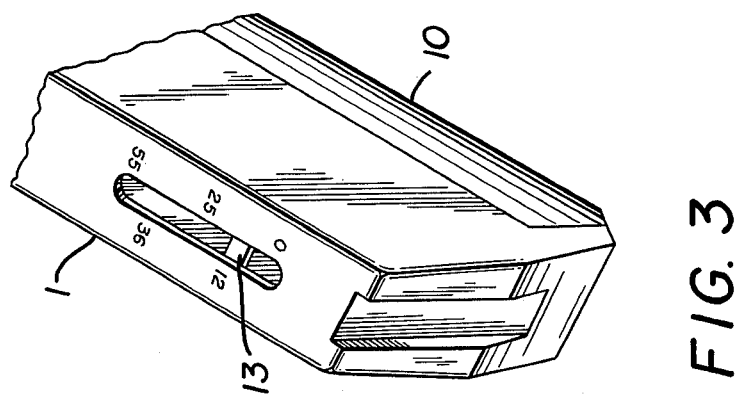
FIG. 3 is a broken perspective view of the front portion of the instrument shown in FIGS. 1 and 2.

FIGS. 1 to 3 describe a surgical stapling instrument having a handle 1 and a trigger 2. A staple forming means is contained in the forward portion of the handle 1. The type of staple forming means is not critical to the practice of this invention. However, a preferred type of forming means is described in U.S. application Ser. No. 191,654 filed Sept. 26, 1980 which is incorporated by reference. The staple forming means includes a staple track 10 which is inserted and attached to the forward portion of the handle 1, for example by cementing or sonic welding. A plurality of staples are internally carried on staple track 10.

Referring to FIG. 6, trigger pivots 2a are placed against stops in the forward portion of the handle 1. The track 10 is then inserted and attached to the handle. The trigger pivots are thus captured.

Referring again to FIGS. 2 and 3, the terminal end of an indicator 13 is visible through an opening in the forward top portion of the handle 1. The initial end of indicator 13 is carried by the staple forming means. The indicator advances one number when a staple is separated from the instrument. A cover 16 (more fully described in FIGS. 4 and 7) is attached to the rear portion of handle 1.

The stapling instrument is used by placing an anvil (not shown but, referring to FIG. 1, located in the lower forward portion of handle 1 and adjacent track 10) adjacent a wound opening or between skin or fascia. The trigger 2 is then compressed into the handle 1. A staple is pushed downward and forced to bend at right angles on either side of the anvil. The forming of a staple around an anvil is well known in the prior art, e.g. as described in U.S. Pat. No. 4,014,492 issued Mar. 29, 1977 which is incorporated by reference. On releasing the trigger and advancing the instrument, the staple is separated from the anvil.

Figure 4:
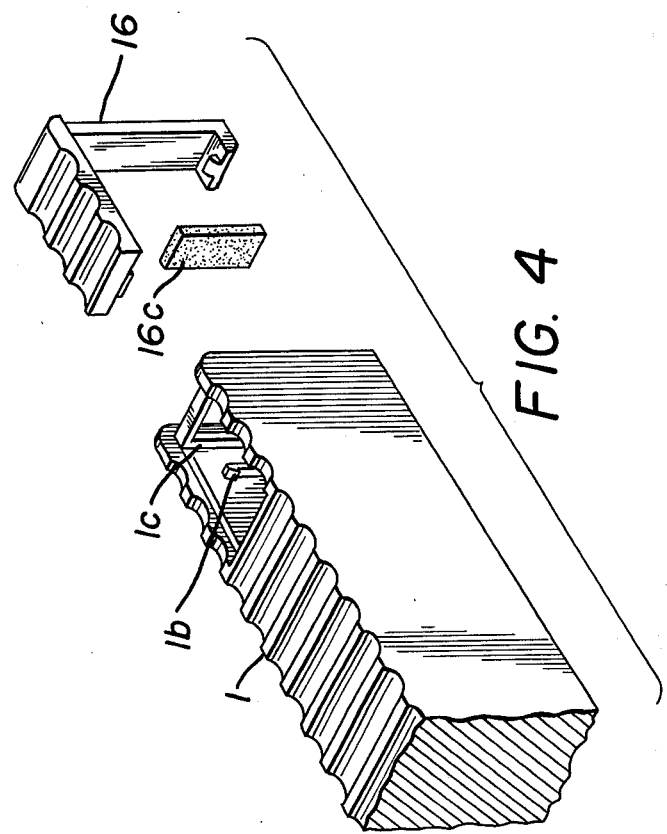
FIG. 4 is an expanded perspective view showing the parts of the stapling instrument control means in the handle and in the handle cover.

Referring to FIGS. 4 to 6, a control means prevents partially compressing the trigger 2, partially forming a staple, and then allowing the trigger to return to its relaxed position and the staple forming means to pick up the next staple. A pad 16a is contained between the cover 16 and a window 1c. As used herein, the term "window" is synonymous with the term "flanged opening". The window 1c is formed of two horizontal and two vertical bars. The width of the window 1c is smaller than the width of the pad 16a. As shown in FIG. 5, the two horizontal bars are offset from the two vertical bars. It is to be understood that the offset of either one or both of the horizontal bars can be approximately limited to the width of the window. To provide a greater frictional surface, either one or both of the abutting surfaces of the pad 16a and the window 1c can be textured, or can be coated with a known anti-slip composition.

A retainer 2c and guide pins 2b are built into the trigger 2. Cam guides 1b are built into handle 1. The contact surface angle of the cam guides 1b can be tangential to the arc of travel of the guide pins 2b. When the trigger 2 is compressed, the guide pins 2b engage the cam guides 1b. The guide pins 2b are biased away from the pad 16a by the construction and orientation of the arm 2e. When the trigger is compressed, the cam guides 1b force the retainer 2c into contact with the pad 16a.

The guide pins 2b are spring loaded. When the trigger is sufficiently compressed, the guide pins cross over the top of the cam guides 1b. Thus, the trigger 2 is released and the retainer 2c is prevented from permanently locking on the pad 16a.

The terminal end of the retainer 2c can be flat. A flat configuration provides a digging effect if trigger compression is stopped. Alternately, a flat configuration provides a smooth surface against the pad 16a during trigger compression. The contact surface angle of the pad 16a can be tangential to the arc of travel of the retainer 2c.

Referring specifically to FIG. 5, the relationship of the pad 16a to the window 1c relationship of the guide pins 2b to the cam guides 1b is offset. In a model, prototype or commercial embodiment, the pad 16a will abut and be contained by the window 1c.

Referring to FIGS. 5 and 6, a stop 2d is contained on the rearward top portion of the trigger 2. The stop arrests the compression force of the trigger 2 into the handle 1. Referring specifically to FIGS. 5 and 7, the stop 2d does not contact the forward tab 16b in the handle cover 16. Rather, the stop 2d is of a sufficient height and distance from the forward tab 16b to contact an interior top portion of the handle 1.

We claim:

1. A surgical stapling control means comprising a handle; a trigger pivotally attached and compressible into said handle; a staple forming means contained in the forward portion of said handle; a flexible arm mounted on the rearward portion of said trigger; a pawl and at least one guide pin attached to one end of said arm; a pad attached to the rearward portion of said handle; and guide means having upper and lower portions, said guide means positioned adjacent the rearward portion of said handle so as to coordinate with and provide tension to said guide pin, such that on partially compressing said trigger the lower portion of said guide means provides tension on said guide pin and flexes said arm such that the pawl engages said pad and such that on complete compression of said trigger, the upper portion of said guide means releases tension from said guide pin allowing said arm to relax and allowing said guide pin to cross over said guide means, thus causing said pawl to be disengaged from said pad.

2. The surgical stapling control means of claim 1 wherein the lower portion of said guide means comprises two cams attached to each side of said handle.

3. The surgical stapling control means of claim 2 wherein two guide pins are attached to one end of said arm and coordinate with said cams.

4. A stapling control means of claim 1 or 2 or 3 wherein said pad is contained between a flanged opening and a handle cover.

5. A stapling control means of claim 4 wherein the surface of the flange adjacent to said pad is textured.

6. A stapling control means of claim 1 or 2 or 3 containing an indicator having a terminal end visible in said handle and an inital end carried by said forming means.

* * * * *